(12) United States Patent
Sun et al.

(10) Patent No.: US 8,580,997 B2
(45) Date of Patent: Nov. 12, 2013

(54) PROCESS FOR PREPARING R-BETA-AMINO PHENYLBUTYRIC ACID DERIVATIVES

(75) Inventors: Piaoyang Sun, Jiangsu (CN); Yongjiang Chen, Jiangsu (CN); Guangliang Yu, Jiangsu (CN)

(73) Assignee: Jiangsu Hengrui Medicine Co. Ltd., Jiangsu (CN)

( * ) Notice: Subject to any disclaimer, the term of this patent is extended or adjusted under 35 U.S.C. 154(b) by 364 days.

(21) Appl. No.: 13/055,385

(22) PCT Filed: Apr. 14, 2009

(86) PCT No.: PCT/CN2009/071259
§ 371 (c)(1),
(2), (4) Date: Jan. 21, 2011

(87) PCT Pub. No.: WO2010/009630
PCT Pub. Date: Jan. 28, 2010

(65) Prior Publication Data
US 2011/0130587 A1    Jun. 2, 2011

(30) Foreign Application Priority Data

Jul. 23, 2008   (CN) .......................... 2008 1 0134472

(51) Int. Cl.
*C07C 261/00* (2006.01)
(52) U.S. Cl.
USPC .......................................................... 560/24
(58) Field of Classification Search
USPC .......................................................... 560/24
See application file for complete search history.

(56) References Cited

U.S. PATENT DOCUMENTS

| | | | |
|---|---|---|---|
| 5,296,482 A | 3/1994 | Peglion et al. | |
| 7,385,080 B2 | 6/2008 | Nohira | |
| 2003/0045555 A1* | 3/2003 | Rivera et al. | 514/351 |

FOREIGN PATENT DOCUMENTS

| | | |
|---|---|---|
| CN | 1371356 A | 9/2002 |
| CN | 1845674 A | 10/2006 |
| WO | WO 2004/085661 A2 | 10/2004 |
| WO | WO 2005/020920 A2 | 3/2005 |

OTHER PUBLICATIONS

Kim et al., Bioorganic and Medicinal Chemistry Letters, 17 (2007) p. 3373-3377.*
J. Am. Chem. Soc. 1986, 108 (22), pp. 7117-7119.
J. Am. Chem. Soc. 1987, 109 (19), pp. 5856-5858.

* cited by examiner

*Primary Examiner* — Johann R Richter
*Assistant Examiner* — Blaine G Doletski
(74) *Attorney, Agent, or Firm* — Brinks Hofer Gilson & Lione; Ryan L. Marshall

(57) ABSTRACT

Disclosed is a process for preparing single enantiomers of beta-amino phenylbutyric acid derivatives and pharmaceutically acceptable salts thereof, which affords the desired compounds having special optical configuration. The process comprises a step of chemical synthesis and a step of resolving the optical isomers of beta-amino phenylbutyric acid derivatives with a resolving agent. The resolving step comprises reacting the optical isomers with resolving agents, such as di-para-toluoyl-L-tartaric acid and di-para-toluoyl-D-tartaric acid. The obtained R-beta-amino phenylbutyric acid derivatives (I) have high optical purity, and the total yield of the accumulative resolution of the laevo and the dextro isomer is up to above 70%.

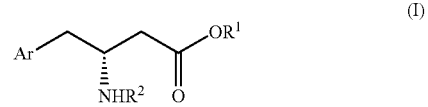

28 Claims, No Drawings

PROCESS FOR PREPARING R-BETA-AMINO PHENYLBUTYRIC ACID DERIVATIVES

The present application is the national phase application of PCT Application No. PCT/CN2009/071259, filed Apr. 14, 2009, which claims priority to Chinese Patent Application No. 200810134472.0, filed Jul. 23, 2008, the entireties of all of which are hereby incorporated by references.

FIELD OF THE INVENTION

The present invention relates to a process for preparing R-beta-amino-phenylbutyric acid derivatives (I) by a chemical synthesis including a resolving process. The compound of formula (I) prepared according to the method of the present invention can be used for the synthesis of a variety of chiral drugs.

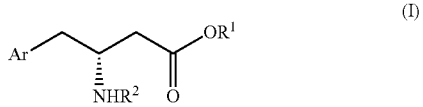

(I)

BACKGROUND OF THE INVENTION

With the development of drug synthesis, more and more chiral drugs are synthesized as single enantiomers. R-beta-Amino-phenylbutyric acid derivatives, which are important chiral pharmaceutical intermediates, usually can be prepared by chiral catalyzed reductions. This method has been reported by several references. For example, a synthetic route of the above mentioned product is disclosed in J. Am. Chem. Soc, 1987, 5856. 2,4,5-Trifluorophenyl acetyl acetoacetate is used as a starting material and Ru-(s)-BINAP is used as a chiral catalyst, and then the beta-hydroxy-2,4,5-trifluorophenyl butyric acid acetate is obtained. Subsequently, the R-beta-amino-phenylbutyric acid acetate can be prepared by the amination of the beta-hydroxy-2,4,5-trifluorophenyl butyric acid acetate. A process for the preparation of chiral R-beta-amino-phenylbutyric acid derivatives is disclosed in J. Am. Chem. Soc, 1986, 7117, using different ligands as reduction catalysts. The patent application WO2004085661 also discloses a synthetic route of R-beta-amino-phenylbutyric acid derivatives. The patent application discloses a method for the preparation of the above chiral intermediates as follows: S-alpha-phenylglycine amide is reacted with 2,4,5-trifluorophenyl acetyl amide to obtain alpha, beta-unsaturated beta-amino-2,4,5-trifluorophenylbutyric acid derivatives containing a chiral center, and then alpha, beta-unsaturated beta-amino-2,4,5-trifluorophenylbutyric acid derivatives are reduced in the presence of platinum oxide ($PtO_2$) catalyst to obtain chiral beta-amino-phenylbutyric acid derivatives. The patent application WO2005020920 discloses a method for the preparation of the compounds of formula (I) by reducing alpha, beta-unsaturated beta-amino-2,4,5-trifluorophenylbutyric acid derivatives, using chloro(1,5-cyclooctadiene) rhodium (I) dimer ([Rh(cod)Cl]$_2$) and (R,S)t-butyl Josiphos as catalysts.

The preparations of beta-amino-phenylbutyric acid derivatives by chiral reductions have been reported by several references, but the results are not satisfactory. First, the chiral reduction catalysts used in these methods are commonly expensive, which substantially leads to high costs. In practice, the homogeneous catalysis is likely to produce the targeted product with a high optical purity. However, the recycling of the homogeneous catalyst is difficult, resulting in high costs, which makes the synthetic route valueless for industrial productions. Second, the condition of the chiral reduction is generally harsh, the chiral catalysts are hard to prepare, and the process is relatively complicated. Third, because the selectivity of the chiral catalysts is often low, the optical purity of the product is not satisfactory. Several re-crystallization steps are needed to prepare the desired product and the process is not suitable for industrial productions. In contrast, a method for the preparation of single enantiomers of the targeted products using resolving agents demonstrates the advantages in all above respects.

So far, the preparation of the R-beta-amino-phenylbutyric acid derivatives by using resolving agents has not been reported in the references. In view of the pharmaceutical value of beta-amino-phenylbutyric acid derivatives, it is necessary to find an effective resolving method to obtain the R-configuration of beta-amino-phenylbutyric acid derivatives as above mentioned with a high optical purity, in high efficiency and high yields.

DETAILED DESCRIPTION OF THE INVENTION

In order to overcome the drawbacks of the prior art, the goal of the present invention is to offer a process for the preparation of R-beta-amino-phenylbutyric acid derivatives of formula (I):

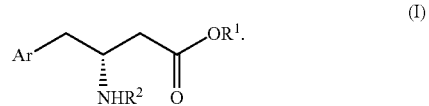

(I)

Ar is unsubstituted phenyl or phenyl substituted with one to five substituents selected from the group consisting of fluorine, methyl, trifluoromethyl and trifluoromethoxy. $R^1$ is hydrogen or $C_{1-6}$ alkyl. $R^2$ is hydrogen or an amino-protecting group, such as alkoxycarbonyl and acyl groups, wherein the alkoxycarbonyl is selected from the group consisting of methoxycarbonyl, ethoxycarbonyl and tert-butoxyl carbonyl, and the acyl is selected from the group consisting of formyl, acetyl, chloroacetyl, trichloroacetyl, benzoyl and phenyl acetyl group. The method comprises the following steps of:

(1) reacting ammonium formate with unsubstituted or substituted phenyl ethyl acetoacetate to obtain an imine, and then reacting the imine with a reducing agent to obtain a racemate of beta-amino-phenylbutyric acid ester;

(2) reacting the racemate of beta-amino-phenylbutyric acid ester and a resolving agent to form a salt of R-form in an alcoholic solvent or an alcohol aqueous solution, and crystallizing the salt; and (3) hydrolyzing the salt of R-form formed from the beta-amino-phenylbutyric acid ester and the resolving agent, or protecting the amino group of the beta-amino-phenylbutyric acid ester to obtain R-beta-amino-phenylbutyric acid derivative of formula (I).

One embodiment of the present disclosure further comprises that R-beta-amino-phenylbutyric acid derivatives of formula (I) obtained in the step (3) is reacted with hydrochloride acid to obtain a hydrochloric acid salt.

The chiral pharmaceutical intermediates, R-beta-amino-phenylbutyric acid derivatives of formula (I) disclosed in the present invention may be prepared as outlined in the following scheme:

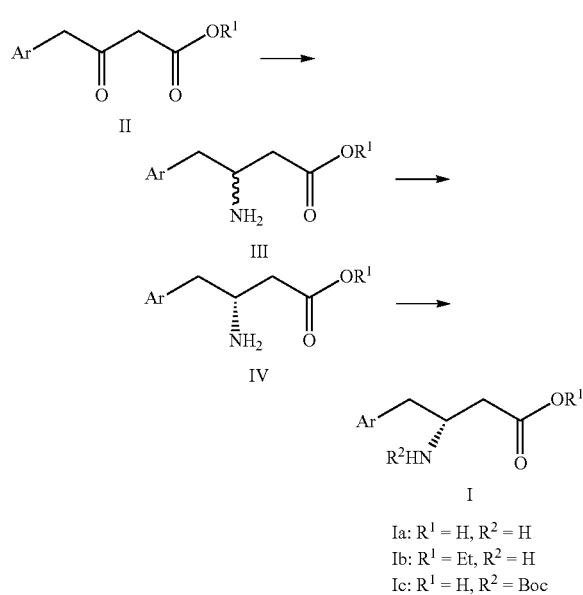

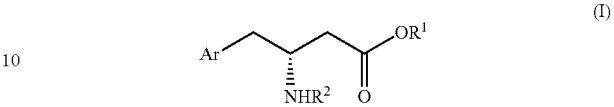

Ia: $R^1 = H, R^2 = H$
Ib: $R^1 = Et, R^2 = H$
Ic: $R^1 = H, R^2 = Boc$

Preferably, in the first product (Ia): Ar is 2,4,5-trifluorophenyl, $R^1$ and $R^2$ are hydrogen.

Preferably, in the second product (Ib): Ar is 2,4,5-trifluorophenyl, $R^1$ is ethyl, and $R^2$ is hydrogen.

Preferably, in the third product (Ic): Ar is 2,4,5-trifluorophenyl, $R^1$ is hydrogen, and $R^2$ is tert-butoxyl carbonyl.

In order to better illustrate the essence of the invention, taking a representative process of the preparation of chiral pharmaceutical intermediates, preferably R-beta-amino-2,4,5-trifluorophenylbutyric acid or pharmaceutically acceptable salts thereof as examples, the present invention is gradually set forth.

A process for the preparation of R-beta-amino-2,4,5-trifluorophenylbutyric acid comprises the following steps.

First, ammonium formate is reacted with a starting material, 2,4,5-trifluorophenyl ethyl acetoacetate to obtain an imine. Then, the imine is reduced by sodium cyanoborohydride to obtain a racemate of beta-amino-phenylbutyric acid ester. Second, R-beta-amino-phenylbutyric acid ester and a resolving agent form a salt of R-form in an alcoholic solvent or an alcohol aqueous solvent. The salt of R-beta-amino-phenylbutyric acid ester is crystallized. Third, the salt is hydrolyzed, or protected the amine group to obtain R-beta-amino-phenylbutyric acid derivatives of formula (I) or pharmaceutically acceptable salts thereof.

In one embodiment of the present invention, the reducing agent used in the step (1) is sodium cyanoborohydride. The chiral resolving agent used in the step (2) is a chiral diacylated tartaric acid comprising: dibenzoyl-D-tartaric acid, dibenzoyl-L-tartaric acid, di-p-toluoyl-D-tartaric acid or di-p-toluoyl-L-tartaric acid.

Preferably, the chiral resolving agent is di-p-toluoyl-D-tartaric acid or di-p-toluoyl-L-tartaric acid.

The resolving agent, di-p-toluoyl-L-tartaric acid or di-p-toluoyl-D-tartaric acid used in the process of the present invention can be used alone or jointly.

Furthermore, in the process of the preparation of R-beta-amino-phenylbutyric acid derivatives, the alcoholic solvent used in the step (2) is a lower fatty alcohol with three or less carbon atoms. Preferably, it is methanol.

In one embodiment of the present invention, the alcoholic aqueous solution used in the step (2) is an aqueous solution of a lower fatty alcohol with less three carbon atoms.

In summary, the problem to be solved by the present invention is to prepare single enantiomers of formula (I) by a chemical synthesis. The process comprises resolving the racemate of beta-amino-phenylbutyric acid derivatives with a resolving agent.

In the reaction scheme mentioned above, compound (II), ($R^1$ is $C_{1-6}$ alkyl or hydrogen) can be prepared according to U.S. Pat. No. 5,296,482. 2,4,5-Trifluoro bromobenzene used as a starting material is alkylated by diethyl malonate. Then, the alkylated product is hydrolyzed and decarboxylated to obtain 2,4,5-trifluoroacetic acid. The acid is condensed with Meldrum's acid. Then, the condensation product is alcoholyzed and decarboxylated by heating the reaction mixture to obtain 2,4,5-trifluorophenyl ethyl acetoacetate, which can be used as the starting material for the preparation of the product of formula (I).

2,4,5-Trifluorophenyl acetyl acetoacetate (II) ($R^1$ is ethyl) is reacted with ammonium formate to obtain an imine. Then, the imine is reduced by sodium cyanoborohydride to obtain the compound (III) ($R^1$ is ethyl). The compound (III) is resolved with a resolving agent to obtain the compound (IV) ($R^1$ is ethyl). Then, the compound (IV) is hydrolyzed, or the amine group of the compound (IV) is protected to obtain the product (I). When $R^1$ and $R^2$ are different groups as shown in the above scheme, the product (I) containing different substituents can represent the specific compound in the various steps, such as (Ia), (Ib) and (Ic) illustrated as above.

After an extensive study, the inventors have found that various commonly used acidic resolving agents are substantially ineffective for the resolution of the racemate of formula (III) in the above resolving process, except that R-camphor sulfonic acid has certain selectivity. Some acidic resolving agents cannot react with the racemate of formula (III) to form crystalline precipitates in solvents effectively. Some acidic resolving agents can react with the racemate of formula (III) to form crystalline precipitates in solvents, but there is no selectivity and the resulting precipitates are still a racemic mixture. After doing some research, the inventors have identified that the ineffective resolving agents include L-tartaric acid, R-mandelic acid, N-acetyl-L-glutamic acid, L-leucine and the like.

Further, the inventors have found that, among a large number of conventional acidic resolving agents tested, only tartaric acids diacylated by benzoyl or substituted benzoyl, such as dibenzoyl-L-tartaric acid (L-DBTA), dibenzoyl-D-tartaric acid (D-DBTA), di-p-toluoyl-L-tartaric acid (L-DTTA) or di-p-toluoyl-D-tartaric acid (D-DTTA), can resolve the (R) configuration and (S) configuration of beta-amino-phenylbutyric acid derivatives effectively.

Generally, the present invention relates to a process for the preparation of R-beta-amino-phenylbutyric acid derivatives (I). The process not only comprises the step of the chemical preparation of a racemate of formula (III), but also comprises the step of reacting a resolving agent with the racemate of formula (III) to obtain the corresponding salt in an alcoholic solvent or an alcohol aqueous solution, and crystallizing the corresponding salt to obtain R-beta-amino-phenylbutyric acid derivatives of formula (I) or corresponding S-beta-amino-phenylbutyric acid derivatives. The resolving agent is dibenzoyl-L-tartaric acid (L-DBTA), dibenzoyl-D-tartaric acid (D-DBTA), di-p-toluoyl-L-tartaric acid (L-DTTA) or di-p-toluoyl-D-tartaric acid (D-DTTA), and preferably di-p-toluoyl-L-tartaric acid or di-p-toluoyl-D-tartaric acid.

In order to obtain single enantiomers of the compounds of formula (I), such as R-configuration of (Ib), 1 mol of D-DTTA is reacted with 2 mol of the racemate of formula (III) ($R^1$=ethyl) in methanol to obtain the corresponding salt. The corresponding salt is crystallized to obtain the crystals with R-configuration (IV) ($R^1$=ethyl). The R-configuration of compound (Ib) is obtained from crystals. On the contrary, when L-DTTA is used as a resolving agent, S-configuration product is obtained.

Further, the resolving process of the present invention includes a re-crystallizing step after the steps of forming and crystallizing the salt. The resolving agent, di-p-toluoyl-L-tartaric acid (L-DTTA) and di-p-toluoyl-D-tartaric acid (D-DTTA) used in the present invention, may be used alone or jointly. Specifically, the present invention relates to a process for preparing and resolving of the intermediates, beta-amino-phenylbutyric acid derivatives of formula (I). The problem to be solved by the present invention is to obtain the above pharmaceutically acceptable optical pure compound of formula (I) of R-configuration with a good yield by using di-p-toluoyl-L-tartaric acid. The method is characterized in that the racemate of formula (III) is reacted with an acidic resolving agent in a particular solvent to obtain the corresponding salt and selectively precipitate the crystals of the salts of the desired chiral intermediate, beta-amino-phenylbutyric acid derivatives.

The method of resolving the intermediate amine of formula (III) includes the process of reacting the intermediate amine of formula (III) with a chiral resolving agent to obtain the corresponding salt, re-crystallizing the corresponding salt to form crystal precipitates and extracting the re-crystallized precipitates to obtain the intermediate amine of formula (Ib). The resolving method can further comprise the step of hydrolyzing (Ib) to obtain (Ia) or protecting the amine group to obtain (Ic). All of the chiral pharmaceutical intermediates can be used for the synthesis of a variety of active pharmaceutical compounds.

With regard to the amount of the resolving agent, in theory, because an acid-base neutralization reaction needs equal numbers of moles of acid and base, the molar ratio of the amines to the resolving agent can be 2:1. If the salt with the certain configuration is desired, the molar ratio can be 4:1. If acid addition salts with equal molar amounts of acid and base are desired, the molar ratio can be 1:1. However, after doing some research, the inventors found that a higher proportion of the resolving agent gives more satisfactory yields of a resolving product with high chiral purity. Generally speaking, the suitable molar ratio of amine intermediates to the resolving agent can be from 4:1 to 1:1, the preferable molar ratio is 2:1 to 1:1. Excessive amount of the resolving agent does not improve the resolution.

The resolving process of a racemate of formula (III) can be carried out in a conventional solvent. Preferably, the process is in an organic solvent, more preferably in an alcoholic solvent. The alcoholic solvent could be used alone or in combination with other organic solvents. Alcoholic solvents used in the present invention include alcoholic solvents used alone as well as alcohol-base mixed solvents. The alcoholic solvent can be a lower fatty alcohol with three or less carbon atoms. Preferably, the solvent is methanol. The alcoholic aqueous solution can be aqueous solution of a short-chain alcohol mentioned above.

In order to improve the chiral purity of the amines of formula (I), sometimes it is necessary to recrystallize the resolving salt obtained. The resolving process can generally be carried out at room temperature; if necessary, under heating conditions. Generally, the re-crystallizing step is carried out under heating condition. First, the salt obtained from the resolution is dissolved in a particular solvent and then re-crystallization is completed slowly at room temperature. In general, after re-crystallizing twice, the chiral purity is often satisfactory, and the ee value is generally above 99%.

The process to obtain the free intermediate is conventional wherein the base used is preferably sodium bicarbonate. The extracting solvent can be a hydrophobic organic solvent used in conventional extractions, such as ethyl acetate, methylene chloride and chloroform, etc., preferably ethyl acetate and chloroform. The process of hydrolyzing the compound of formula (I) is also conventional, and the base used is preferably sodium hydroxide. The acid used in the salt formation is preferably hydrochloride acid. The salt formation method is conventional. It can be readily performed by a person with ordinary skill in the art.

The optical purity of the ester or acid of the compound formula (I) according the present invention is more than 99%, particularly suitable as a synthetic intermediate of chiral drugs.

Preferred Embodiments

The present invention is illustrated by the following examples in detail, which should not be construed as limiting the scope of the present invention.

PREPARATION EXAMPLE 1

114 g (0.60 mol) of 2,4,5-trifluorophenylacetic acid was dissolved in 600 mL of THF. To this mixture, 107 g (0.66 mol) of carbonyldiimidazole was added with stirring (when a part of carbonyldiimidazole was added, a lot of solid was formed; subsequently, the solid thereby dissolved in the solution with further addition). Upon completion of the addition, the reaction mixture was warmed to 50° C. 95.1 g (0.66 mol) of Meldrum's acid was added, and the mixture was aged for 3 hours at 50° C. The mixture was concentrated to remove THF and the residue was dissolved in water (600 mL) and dichloromethane (800 mL), and then the pH value was adjusted to 2. The aqueous phase was separated and the organic phase was washed with 0.1N HCl and water (600 mL) respectively. The organic phase was dried and concentrated to obtain 182 g of a condensate, 5-[2-(2,4,5-trifluorophenyl)-acetyl]-2,2-dimethyl-1,3-dioxane-4,6-dione, as a solid (the re-crystallization can be carried out in ethyl acetate to obtain a white solid). Melting point: 101.5-103.5° C., Yield: 96%.

EXAMPLE 1

60 g of the condensate (0.190 mol) obtained from the preparation example 1 was dissolved in ethanol (600 mL). The mixture was stirred at 70° C. for 3 hours, and a solution of 2,4,5-trifluorophenyl ethyl acetoacetate in ethanol was obtained. 70 g of formic acid (1.11 mol) was added to the mixture, and the reaction mixture was heated to reflux for 3 hours. After cooling to 40° C., 15 g of sodium cyanoborohydride (0.239 mol) was added slowly to the reaction mixture, and the reaction mixture was heated to reflux for 2 hours. After cooling, the mixture was concentrated to remove ethanol and the residue was dissolved in water, the pH value was adjusted to 9. The mixture was extracted with dichloromethane and washed with a small amount of water. The organic phase was dried and concentrated to obtain 45 g of beta-amino-phenylbutyric acid ethyl ester as a brown oil. Yield: 90.5%.

EXAMPLE 2

5.18 g (20 mmol) of the racemate of beta-amino-phenylbutyric acid ethyl ester was dissolved in methanol (60 mL), and 3.86 g (10 mmol) of D-DTTA was added with stirring. A lot of white solid precipitated quickly from the reaction solution. The mixture was heated to reflux for 1-2 hours (the solid was not completely dissolved in the solution). After cooling to below 10° C., the resulting precipitates were collected by filtration and washed with a small amount of methanol, and then the re-crystallization was carried out in methanol. After re-crystallizing twice, 3.37 g of a white powder was obtained. Melting point: 187.0-188.0° C., $[a]_D^{25}=+96.7°$ (C1, 0.1 M NaOH). 3.0 g of the white solid was treated with a base to obtain 1.20 g of R-beta-amino-phenylbutyric acid ethyl ester (Ib). The optical purity of (Ib) was more than 99.7%, and the first resolving yield was 52.2%.

The resulting residual solutions during the above resolving process and the twice re-crystallization processes were combined and then concentrated to dryness to obtain a crude product. The crude product was treated with saturated sodium bicarbonate to obtain the free amine. The solution was extracted with chloroform to obtain 4.7 g of a racemate mainly composed of S-configuration. HPLC analysis showed 71.3% of S-configuration. The racemate was dissolved in methanol (60 mL), and 3.86 g of L-DTTA (10 mmol) was added for inverse resolution. The mixture was heated to reflux until a clear solution was obtained. After cooling, crystals precipitated from the reaction solution. The resulting precipitates were collected by filtration and then were dried to obtain a crude product. HPLC analysis showed 95.6% of S-configuration. The crude product of S-configuration was dissolved in 60 mL of methanol, and the mixture was heated to reflux until a clear solution was obtained. After cooling, crystals precipitated from the solution. The resulting precipitates were collected by filtration and then dried to obtain 3.44 g of a salt of L-DTTA of S-configuration. Melting point: 182.0-183.5° C., $[a]_D^{25}=-90.3°$ (C1, 0.1 M NaOH). The reverse resolving yield was 53.3%. HPLC analysis showed 98.4% of S-configuration.

The residual solution during the above reverse resolving process and re-crystallization process was combined, and then concentrated to dryness to obtain a crude product. The crude product was treated with saturated sodium bicarbonate to obtain the free amine. The solution was extracted with chloroform to obtain 1.9 g of a racemate composed of mainly of R-configuration. HPLC analysis showed 67.4% of R-configuration. The racemate was dissolved in 20 mL of methanol, and 1.5 g of D-DTTA was added. The mixture was heated to reflux until a clear solution was obtained. After cooling, crystals precipitated from the resolution. The precipitate was collected by filtration and dried to obtain 0.92 g of a salt. HPLC analysis showed 99.30% of R-configuration. The resulting salt was treated with saturated sodium bicarbonate to obtain the free amine. The solution was extracted with chloroform to obtain 0.5 g of the intermediate amine (Ib) of R-configuration. Yield: 19.5%. HPLC analysis showed 99.3% of R-configuration. The total resolving yield was 71.4%.

EXAMPLE 3

5.18 g (20 mmol) of the racemate of beta-amino-phenylbutyric acid ethyl ester was dissolved in methanol (60 mL), and 3.86 g (10 mmol) of L-DTTA was added with stirring. A lot of white solid precipitated quickly from the reaction solution. The mixture was heated to reflux for 1-2 hours (the solid was not completely dissolved in the solution). After cooling to below 10° C., the resulting precipitates were collected by filtration and washed with a small amount of methanol. The residual solution was concentrated to dryness and 70 mL of water was added, the pH value was adjusted to 8 with a saturated sodium bicarbonate solution. The mixture was extracted with dichloromethane. The organic phase was washed with water and concentrated to obtain an oil product.

The oil product was dissolved in methanol (60 mL), and 3.86 g of D-DTTA (10 mmol) was added with stirring. A lot of white solid precipitated quickly from the reaction solution. The mixture was heated to reflux for 1-2 hours (the solid was not completely dissolved in the solution). After cooling to below 10° C., crystals precipitated from the solution. The resulting precipitates was collected by filtration and washed with a small amount of methanol, and then the re-crystallization was carried out in methanol. After re-crystallization, 4.17 g of a white powder was obtained. Melting point: 185.0-186.5° C., $[a]_D^{25}=+95.8°$ (C1, 0.1 M NaOH). 4.0 g of the white solid was treated with a base to obtain 1.61 g of R-beta-amino-phenylbutyric acid ethyl ester (Ib). The optical purity of Ib was more than 99.7% and the resolving yield was 64.8%.

EXAMPLE 4

5.18 g (20 mmol) of the racemate of beta-amino-phenylbutyric acid ethyl ester was dissolved in ethanol (120 mL), and 3.86 g of D-DTTA (10 mmol) was added with stirring. The mixture was heated to reflux until a clear solution was obtained. After cooling, crystals precipitated from the solution. The resulting precipitates were collected by filtration and dried to obtain the crude product. HPLC analysis showed 89.4% of R-configuration.

The re-crystallization of the crude product carried out in ethanol (120 mL). After re-crystallization twice, 2.82 g of a white solid was obtained. Melting point: 186.0-187.0° C., $[a]_D^{25}=+96.4°$ (C1, 0.1 M NaOH). HPLC analysis showed 99.1% of R-configuration. The white solid was dissolved in 20 mL of water, and the pH value was adjusted to 8-9 with anhydrous sodium carbonate. The mixture was extracted with dichloromethane twice (10 mL×2). The organic phase was combined and washed with water, the organic phase was concentrated to dryness to obtain 1.13 g of R-beta-amino-2,4,5-trifluorophenylbutyric acid ethyl ester (Ib). $[a]_D^{25}=-2.6°$ (C=0.8, methanol). The resolving yield was 43.6%.

EXAMPLE 5

5.18 g (20 mmol) of the racemate of beta-amino-phenylbutyric acid ethyl ester was dissolved in ethanol (100 mL), and 3.58 g of D-DBTA (10 mmol) was added with stirring. The mixture was heated to reflux until a clear solution was obtained. After cooling, crystals precipitated from the solution. The resulting precipitates were collected by filtration and dried to obtain the crude product. HPLC analysis showed 83.37% of R-configuration.

The re-crystallization of the crude product carried out in ethanol (100 mL). After re-crystallization twice, 2.59 g of a white solid was obtained. HPLC analysis showed 99.2% of R-configuration. The white solid was dissolved in 18 mL of water, and the pH value was adjusted to 8-9 by anhydrous sodium carbonate. The mixture was extracted with dichloromethane twice (10 mL×2). The organic phase was combined and washed with water, the organic phase was concentrated to dryness to obtain 1.03 g of R-beta-amino-2,4,5-trifluorophenylbutyric acid ethyl ester (Ib). [a]$_D^{25}$=−2.7° (C=0.8, methanol). The resolving yield was 39.8%.

EXAMPLE 6

1 g (3.84 mmol) of R-beta-amino-2,4,5-trifluorophenylbutyric acid ethyl ester (Ib) was added to the mixture of methanol (10 mL) and sodium carbonate aqueous solution (10 mL), in which the pH value was 10, and then 1.0 g of (BOC)$_2$O was added. The reaction mixture was reacted at 30° C. for 3 hours. After the reaction was completed, 4 M NaOH (8 mL) was added to the mixture. The hydrolyzation was carried out at 40-45° C. After 2 hours, the reaction was detected by TLC. The solvent was evaporated, and the pH was slowly adjusted to 3. The mixture was extracted with ethyl acetate and washed with acidic water. The organic phrase was dried and concentrated, and then crystals precipitated to obtain 1.14 g of R-beta-t-butoxyl carbonyl amino-2,4,5-trifluorophenylbutyric acid (Ic). Melting point: 127-128° C. [a]$_D$25=14.2° (C=1, methanol). Yield: 89.1%.

EXAMPLE 7

1.0 g (3.0 mmol) of R-beta-t-butoxyl carbonyl amino-2,4,5-trifluorophenylbutyric acid (Ic) was added to 20 mL of the mixture of ethyl acetate and HCl (2 M). The mixture was stirred for 4 hours at room temperature. The solution was concentrated to half its volume at low temperature, and crystals precipitated from the solution. The resulting precipitates were collected by filtration and dried to obtain 0.67 g of R-beta-amino-2,4,5-trifluorophenylbutyric acid hydrochloride salt (Ia). Melting point: 204.5-207.5° C. [a]$_D^{25}$=−6.8° (C=0.8, methanol). Yield: 82.8%.

EXAMPLE 8

1.0 g of R-beta-amino-2,4,5-trifluorophenylbutyric acid ethyl ester (Ib) (3.84 mmol) was dissolved in 10 mL of methanol, and 4 M sodium hydroxide (6 mL) was added. The hydrolyzation was carried out at 40° C. After 2 hours, the reaction was detected by TLC. The pH value was adjusted to 3, and the solvent was concentrated to dryness. The residue was dissolved in chloroform and methanol (4:1). The undissolved compounds were removed by filtration, and the filtrate was placed on a silica gel column. The main fraction was collected and concentrated to dryness. 16 mL of ethyl acetate was added to the residue and the mixture was stirred for 2 hours at room temperature. Crystals precipitated from the solution and dried to obtain 0.90 g of R-beta-amino-2,4,5-trifluorophenylbutyric acid hydrochloride salt (Ia). Melting point: 203.0-206.0° C. [a]$_D^{25}$=−6.4° (C=0.8, methanol). Yield: 87.1%.

What is claimed is:

1. A process for preparing a single enantiomer of a beta-amino-phenylbutyric acid derivative, comprising:
    reacting ammonium formate with unsubstituted or substituted phenyl ethyl acetoacetate to obtain an imine;
    reducing the imine to obtain a racemate of beta-amino-phenylbutyric acid ester;
    reacting the racemate of beta-amino-phenylbutyric acid ester and a resolving agent to form a salt of the single enantiomer of beta-amino-phenylbutyric acid ester in a solvent; and
    crystallizing the salt of the single enantiomer of beta-amino-phenylbutyric acid ester.

2. The process of claim 1, wherein the resolving agent is a tartaric acid diacylated by benzoyl or substituted benzoyl.

3. The process of claim 2, wherein the resolving agent is selected from the group consisting of dibenzoyl-D-tartaric acid, dibenzoyl-L-tartaric acid, di-p-toluoyl-D-tartaric acid, di-p-toluoyl-L-tartaric acid, and combinations thereof.

4. The process of claims 3, wherein the resolving agent is di-p-toluoyl-D-tartaric acid or di-p-toluoyl-L-tartaric acid.

5. The process of claims 3, wherein the resolving agent is di-p-toluoyl-D-tartaric acid combined with di-p-toluoyl-L-tartaric acid.

6. The process of claims 1, wherein the ratio of the racemate of beta-amino-phenylbutyric acid ester to the resolving agent is from about 4:1 to about 1:1.

7. The process of claims 6, wherein the ratio of the racemate of beta-amino-phenylbutyric acid ester to the resolving agent is from about 2:1 to about 1:1.

8. The process of claim 1, wherein the imine is reduced by sodium cyanoborohydride.

9. The process of claim 1, wherein the solvent is an alcoholic solvent.

10. The process of claim 9, wherein the solvent contains a lower fatty alcohol with three or less carbon atoms.

11. The process of claim 9, wherein the alcoholic solvent is methanol.

12. The process of claim 9, wherein the solvent is an alcoholic and aqueous mixed solvent.

13. The process of claim 1, further comprising:
    hydrolyzing the salt of the single enantiomer of beta-amino-phenylbutyric acid ester to obtain a single enantiomer of beta-amino-phenylbutyric acid.

14. The process of claim 1, further comprising:
    reacting the salt of the single enantiomer of beta-amino-phenylbutyric acid ester with a base to obtain the single enantiomer of beta-amino-phenylbutyric acid ester.

15. The process of claim 14, further comprising
    reacting the single enantiomer of beta-amino-phenylbutyric acid ester with hydrochloric acid to form a hydrochloride salt.

16. The process of claim 14, further comprising:
    protecting the amino group of the single enantiomer of beta-amino-phenylbutyric acid ester with an amino protecting group.

17. The process of claim 16, further comprising:
    removing the amino protecting group to obtain the single enantiomer of beta-amino-phenylbutyric acid ester.

18. The process of claim 1, further comprising:
    re-crystallizing the salt of the single enantiomer of beta-amino-phenylbutyric acid ester.

19. A process for preparing R-beta-amino-phenylbutyric acid derivatives of formula (I),

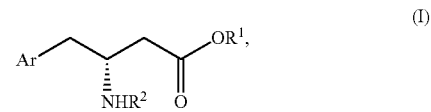

wherein Ar is unsubstituted phenyl or phenyl substituted with one to five substituents selected from the group consisting of fluorine, methyl, trifluoromethyl and trifluoromethoxy; $R^1$ is hydrogen or $C_{1-6}$ alkyl; and $R^2$ is selected from the group consisting of hydrogen, an alkoxycarbonyl group, and an acyl group; and wherein the process comprises:

reacting ammonium formate with unsubstituted or substituted phenyl ethyl acetoacetate to obtain an imine, reducing the imine to obtain a racemate of beta-amino-phenylbutyric acid ester;

reacting the racemate of beta-amino-phenylbutyric acid ester and a resolving agent to form a salt of R-beta-amino-phenylbutyric acid ester in a solvent; and crystallizing the salt of R-beta-amino-phenylbutyric acid ester.

20. The process of claim 19, wherein Ar is 2,4,5-trifluorophenyl.

21. The process of claim 19, wherein $R^1$ is hydrogen.

22. The process of claim 19, wherein $R^1$ is ethyl.

23. The process of claim 19, wherein $R^2$ is hydrogen.

24. The process of claim 19, wherein $R^2$ is an alkoxycarbonyl group.

25. The process of claim 24, wherein the alkoxycarbonyl group is selected from the group consisting of methoxycarbonyl, ethoxycarbonyl and tert-butoxyl carbonyl group.

26. The process of claim 25, wherein $R^2$ is tert-butoxyl carbonyl group.

27. The process of claim 19, wherein the acyl group is selected from the group consisting of formyl, acetyl, chloroacetyl, trichloroacetyl, benzoyl and phenyl acetyl group.

28. A process for preparing R-beta-amino-phenylbutyric acid derivatives, comprising:

reacting ammonium formate with unsubstituted or substituted phenyl ethyl acetoacetate to obtain an imine;

reducing the imine to obtain a racemate of beta-amino-phenylbutyric acid ester;

reacting the racemate of beta-amino-phenylbutyric acid ester and di-p-toluoyl-D-tartaric acid to form a first salt of R-beta-amino-phenylbutyric acid ester in a solvent;

crystallizing the salt to obtain R-beta-amino-phenylbutyric acid ester, and a first residual solution with R-form and S-form thereof;

reacting the first residual solution with a first base to obtain a first freed beta-amino-phenylbutyric acid ester with more S-form than R-form thereof;

reacting di-p-toluoyl-L-tartaric acid with the first freed beta-amino-phenylbutyric acid ester to obtain a salt of S-form;

crystallizing the salt of S-form to obtain the S-form thereof, and a second residual solution with R-form and S-form thereof;

reacting the second residual solution with a second base to obtain a second freed beta-amino-phenylbutyric acid ester with more R-form than S-form thereof;

reacting di-p-toluoyl-D-tartaric acid with the second freed beta-amino-phenylbutyric acid ester to obtain a second salt of R-form; and crystallizing the second salt of R-form to obtain the R-form thereof.

* * * * *